United States Patent

Asselin et al.

[11] 4,454,150
[45] Jun. 12, 1984

[54] 6,7,8,9-TETRAHYDRO-3H-BENZ(E)INDOL-7-AMINES AND A METHOD OF DOPAMINE RECEPTOR STIMULATION THEREWITH

[75] Inventors: André A. Asselin, St. Laurent; Leslie G. Humber, Dollard des Ormeaux, both of Canada

[73] Assignee: Ayerst, McKenna & Harrison Inc., Montreal, Canada

[21] Appl. No.: 312,464

[22] Filed: Oct. 19, 1981

[51] Int. Cl.³ .................... A61K 31/40; C07D 209/60
[52] U.S. Cl. ..................................... 424/274; 548/427
[58] Field of Search ......................... 548/427; 424/274

[56] References Cited

U.S. PATENT DOCUMENTS

| | | | |
|---|---|---|---|
| 4,110,339 | 8/1978 | Bach et al. | 424/274 X |
| 4,212,804 | 7/1980 | Coppola | 548/485 |
| 4,370,341 | 1/1983 | Asselin et al. | 548/427 |

FOREIGN PATENT DOCUMENTS 2044172  8/1970  Fed. Rep. of Germany .

OTHER PUBLICATIONS

L. B. Shagalov et al., Chem. Abstr., 91, 56747 v, (1979), for Khim. Geterotsikl. Soedin, (3), 360, (1979).
L. B. Shagalov et al., Chem. Abstr., 89, 146703 r, (1978), for Khim. Geterotsikl. Soedin, (5), 634, (1978).
Chem. Abs., vol. 69, No. 25, p. 96, Abs. No. 106400, Dec. 16, 1968.

Primary Examiner—Paul M. Coughlan, Jr.
Assistant Examiner—D. B. Springer
Attorney, Agent, or Firm—Arthur E. Wilfond

[57] ABSTRACT

Herein is disclosed compounds of the formula

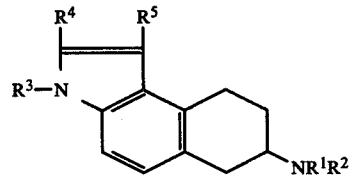

in which $R^1$, $R^2$, $R^3$, $R^4$ and $R^5$ each is hydrogen or lower alkyl, therapeutically acceptable acid addition salts thereof, processes for their preparation, methods of using the compounds and pharmaceutical compositions. The compounds exhibit dopamine-receptor stimulating activity in a mammal and are useful for treating hyperprolactinemia, galactorrhea, amenorrhea, impotence, Parkinsonism, diabetes, acromegaly, hypertension and other central nervous system disorders.

6 Claims, No Drawings

6,7,8,9-TETRAHYDRO-3H-BENZ(E)INDOL-7-AMINES AND A METHOD OF DOPAMINE RECEPTOR STIMULATION THEREWITH

RELATED APPLICATION

Related hereto is U.S. patent application Ser. No. 215,482, filed Dec. 11, 1980, now U.S. Pat. No. 4,370,341.

BACKGROUND OF THE INVENTION

This invention relates to novel 6,7,8,9-tetrahydro-3H-benz[e]indol-7-amine derivatives, to therapeutically acceptable acid addition salts thereof, to processes for their preparation, to methods of using the derivatives and to pharmaceutical compositions of the derivatives. These derivatives exhibit dopamine-receptor stimulating activity in a mammal. Thus, they can be useful for treating hyperprolactinemia, galactorrhea, amenorrhea, impotence, Parkinsonism, diabetes, acromegaly, hypertension and other central nervous system disorders which respond to dopamine-receptor stimulation.

A number of 6,7,8,9-tetrahydro-3H-benz[e]indole derivatives are known and described, for example, L. B. Shagalov et al., Chem. Abstr., 91, 56747 v (1979) for Khim. Geterotsikl. Soedin., (3), 360 (1979); L. B. Shagalov et al., Chem. Abstr., 89, 146703 r (1978) for Khim. Geterotsikl. Soedin., (5), 634 (1978); Derwent Publications Ltd., Farmdoc 46000U for Netherland Pat. No. 7,300,871, published July 30, 1973; and Derwent Publications Ltd., Farmdoc 24087B for German Offenlegenshift No. 2,740,836, published Mar. 22, 1979. The reported compounds lack the substituents on the 6,7,8,9-tetrahydro-3H-benz[e]indole ring system which are characteristic of the compounds of this invention. N. J. Bach and E. C. Kornfeld, U.S. Pat. No. 4,110,339, Aug. 29, 1978 disclose tricyclic tetrahydro-2H-benzo[c]pyrroles which are dopamine agonist. These latter compounds are distinguished most readily from the compounds of this invention by having a perifused tricyclic ring system.

SUMMARY OF THE INVENTION

The compounds of this invention are represented by formula I

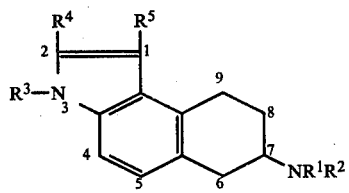

in which $R^1$, $R^2$, $R^3$, $R^4$ and $R^5$ each is hydrogen or lower alkyl having 1 to 5 carbon atoms, or a therapeutically acceptable acid addition salt thereof.

A preferred group of compounds of this invention is represented by formula I in which $R^1$, $R^2$, $R^3$, $R^4$ and $R^5$ each is hydrogen or lower alkyl having 1 to 3 carbon atoms, or a therapeutically acceptable acid addition salt thereof.

Another preferred group of compounds of this invention is represented by formula I in which $R^1$ and $R^2$ each is hydrogen or lower alkyl having 1 to 5 carbon atoms and $R^3$, $R^4$ and $R^5$ are hydrogen, or a therapeutically acceptable acid addition salt thereof.

A most preferred group of compounds of this invention is represented by formula I in which $R^1$ and $R^2$ each is lower alkyl having 1 to 3 carbon atoms and $R^3$, $R^4$ and $R^5$ are hydrogen, or a therapeutically acceptable acid addition salt thereof.

A pharmaceutical composition is provided by admixing the compound of formula I, or a therapeutically acceptable acid addition salt thereof, with a pharmaceutically acceptable carrier.

The compounds of this invention are used to stimulate dopamine receptors in a mammal in need thereof by administering to the mammal an effective dopamine receptor stimulating amount of a compound of formula I or a therapeutically acceptable acid addition salt thereof. The compounds of this invention are favorably used in combination with an effective amount of an agent commonly used in the treatment of Parkinsonism and related disorders, particularly those selected from bromocriptine, lergotrile, levodopa, combination of levodopa and carbidopa, L-prolyl-L-leucylglycinamine and L-prolyl-N-methyl-D-leucylglycinaminde.

The compounds of formula I or a therapeutically acceptable acid addition salt thereof can be prepared by selecting a process from the group of:

(a) when a compound of formula I in which $R^1$ and $R^2$ each is lower alkyl and $R^3$, $R^4$ and $R^5$ are hydrogen is required, reducing a corresponding compound of formula X

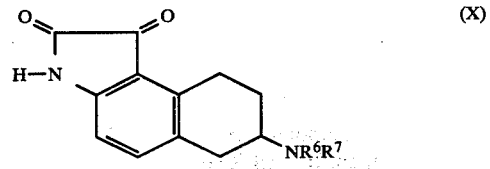

in which $R^6$ and $R^7$ each is lower alkyl with a complex metal hydride;

(b) when a compound of formula I in which $R^1$, $R^4$ and $R^5$ are hydrogen and $R^2$ and $R^3$ each is hydrogen or lower alkyl is required, hydrogenating a compound of formula XI

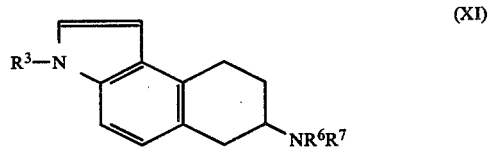

in which $R^3$ is hydrogen or lower alkyl, $R^6$ is benzyl and $R^7$ is benzyl or lower alkyl;

(c) when a compound of formula I in which $R^1$, $R^2$ and $R^4$ each is lower alkyl, $R^3$ is hydrogen and $R^5$ is hydrogen or lower alkyl is required, condensing a compound of formula XII

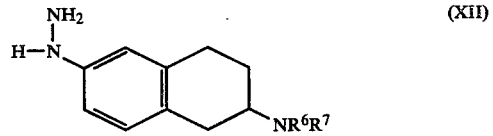

in which R⁶ and R⁷ each is lower alkyl with a ketone of the formula

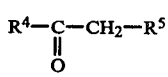

in which R⁴ is lower alkyl and R⁵ is hydrogen or lower alkyl according to the Fischer indole method;

(d) when a compound of formula I in which R¹ is hydrogen, R², R³ and R⁵ each is hydrogen or lower alkyl and R⁴ is lower alkyl is required, hydrogenating a corresponding compound of formula XIV

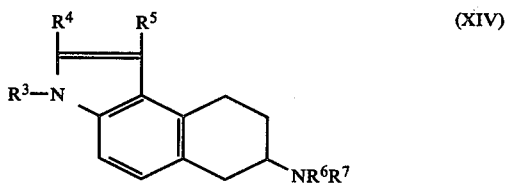

in which R³ and R⁵ each is hydrogen or lower alkyl, R⁴ is lower alkyl, R⁶ is benzyl and R⁷ is benzyl or lower alkyl;

(e) when a compound of formula I in which R¹, R² and R⁵ each is lower alkyl and R³ and R⁴ are hydrogen is required, decarboxylating a corresponding compound of formula XVI

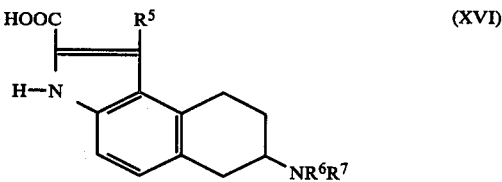

in which R⁵, R⁶ and R⁷ each is lower alkyl;

(f) when a compound of formula I in which R¹ and R⁴ are hydrogen, R² and R³ each is hydrogen or lower alkyl and R⁵ is lower alkyl is required, hydrogenating a corresponding compound of formula XVII

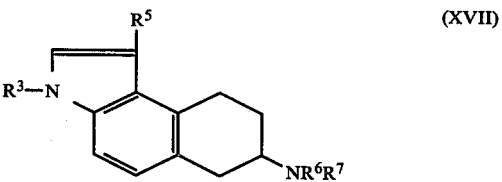

in which R³ is hydrogen or lower alkyl, R⁵ is lower alkyl, R⁶ is benzyl and R⁷ is benzyl or lower alkyl;

(g) when a compound of formula I in which R¹, R² and R³ each is lower alkyl and R⁴ and R⁵ each is hydrogen or lower alkyl is required, alkylating the corresponding compound of formula I in which R¹ and R² each is lower alkyl, R³ is hydrogen and R⁴ and R⁵ each is hydrogen or lower alkyl; and (h) when a therapeutically acceptable acid addition salt of a compound of formula I is required, reacting the compound of formula I with a therapeutically acceptable acid.

DETAILED DESCRIPTION OF THE INVENTION

The term "lower alkyl" as used herein means straight and branched chain alkyl radicals containing from one to five carbon atoms and includes methyl, ethyl, propyl, 1-methylethyl, butyl, 1,1-dimethylethyl and pentyl, unless stated otherwise.

The term "complex metal hydride" as used herein means metal hydride reducing agents and includes, for example, lithium aluminum hydride, lithium aluminum hydride-aluminum chloride, aluminum hydride-aluminum chloride, diborane, diisobutylaluminum hydride, borane methyl sulfide and sodium borohydride-aluminum chloride.

Also included in this invention are the stereochemical isomers of the compounds of formula I which result from asymmetric centers contained therein. These isomeric forms may be prepared by chemical methods and are purified readily by crystallization or chromatography.

Individual optical isomers, which might be separated by fractional crystallization of the diastereoisomeric salts formed thereof, for instance, with d- or l-tartaric acid or D-(+)-α-bromocamphor sulfonic acid, are also included.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic, acetic, maleic, methanesulfonic, malic, citric, or tartaric acid; and acids which are sparingly soluble in body fluids and which impart slow-release properties to their respective salts, e.g., pamoic acid, tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The discovery in the mid-1960's of two major dopamine (DA) systems indicated that this neurotransmitter exerted control over a number of physiological functions. Against this background an interest arose to develop DA receptor agonists to study the function of the dopaminergic systems and to evaluate these agonists as possible therapeutic agents in Parkinson's disease and certain neuroendocrine disorders, for example, hyperprolactinemia, galactorrhea, amenorrhea, impotence, hypertension and other central nervous system disorders.

The DA receptor agonists exert a variety of pharmacological effects, some of the most characteristic being the ones that occur in animals in which DA deficiency is brought about to mimic the Parkinsonian syndrome. An important model was developed by U. Ungerstedt, Acta. Physiol. Scand., Suppl. 367 69–93 (1971) who, by means of unilateral injections of 6-hydroxydopamine (6-OHDA) into the DA pathway, could produce selective lesions of the ascending DA pathways on one side of the brain. Ungerstedt (1971) demonstrated in these lesioned rats that DA receptor agonists induced rotational behavior towards the innervated side. The response is due to the development of receptor supersensitivity in the denervated striatum resulting in a higher degree of DA receptor activity on the denervated- as compared to the innervated-side after treatment with DA receptor agonists. Due to this imbalance between the two sides, a rotational behavior is elicited, the direction being always towards the less activated side. It is of interest that in the discovery of the DA receptor stimulating properties of bromocriptine, the 6-OHDA rotational model was utilized [H. Corrodi et al., J. Pharm. Pharmacol., 25, 409–412 (1973)].

In the test for rotational behavior in rats following the unilateral 6-OHDA-induced destruction of one nigrostriatal pathway, the method described by C. J. Pycock and C. D. Marsden, Europ. J. Pharmacol., 47, 167 (1978) was followed. The rats (230–250 g) were anesthetized with sodium pentobarbital (40 mg/kg i.p.) and intracerebral injections were made using a Stoelting stereotaxic instrument, (C. H. Stoelting Co., Chicago, Ill., U.S.A.). Unilateral injections of 6-OHDA hydrobromide (8 $\mu$g/3 $\mu$l delivered at a rate of 1 $\mu$l per min) were made into the ascending median forebrain bundle (MFB) in the lateral hypothalamus according to the coordinates of the De Groot brain atlas, J. De Groot, Verhandel, Koninkl. Ned. Akad. Wetenschap. Natuurk. 52: 1–40 (1959), (A: +4.6, L: ±1.9, V: −2.7). 6-OHDA was made up in ice-cold distilled water containing 0.2 mg/ml ascorbic acid.

Three weeks after operation, the rats were tested for rotational behavior in response to apomorphine hydrochloride (0.25 mg/kg, s.c.). Rats which consistently showed more than 5 turns/min after apomorphine were selected and the compound of formula I was then administered. The rat was immediately placed in the rotometer, described by K. Voith and J. R. Cummings, Can. J. Pharmacol., 54, 551 (1976), and the rotation was continuously recorded until drug effect subsided. In this test, the following compound of formula I is demonstrated to be an effective dopamine receptor agonist [the amount of the compound, route of administration and total turns±S.E. (standard error) during the time observed are indicated in the parenthesis]: 6,7,8,9-tetrahydro-N,N-dipropyl-3H-benz[e]indol-7-amine (at a subcutaneous dose of 2.5 mg/kg exhibited 2867±269 turns in an 7.5 hour duration).

A recently developed animal model, described by G. P. Smith and R. C. Young in "Advances in Neurology", Vol. 5, F. H. McDowell and A. Barbeau, Eds., Raven Press, New York, pp. 427–432 (1974), shows that rats exhibit almost complete akinesia in an open field following the bilateral injection of 6OHDA into the anterolateral hypothalamus. The compounds of formula I can reverse this 6-OHDA-induced hypokinesia as a result of their functioning as dopamine receptor agonists. In this test for dopamine receptor agonists, the compounds of formula I can exhibit a pharmacological response that is comparable to that of apomophine and bromocriptine.

Experiments are performed on male Sprague-Dawley rats housed in air-conditioned quarters. The room is lighted between 0700 and 1900 hr daily and maintained at a temperature of 24° C.±2° C.

The method of Smith and Young, cited above, is followed. Rats (approximately 280 g) are operated on under sodium pentobarbital anesthesia. Using a Stoelting stereotaxic instrument, the tip of a 26 gauge cannula is positioned in the anterolateral hypothalamus (7 mm anterior to the interaural line, 2 mm lateral to the midline and 8 mm below the dura) according to the De Groot brain atlas, noted above. Via a polyethylene tubing (PE 20), the cannula is connected to a 10 $\mu$l syringe which is mounted in a Starrett micrometer head drive, C. H. Stoelting Co., Chicago, Ill., U.S.A. All injections are bilateral. Each injection consisted of 4 $\mu$l of distilled water containing 6-OHDA (6.5 $\mu$g base/$\mu$l) and ascorbic acid (0.4 $\mu$g/$\mu$l).

The animals have free access to Purina Laboratory Chow pellets and tap water. However since anterolateral hypothalamic 6-OHDA injections produce aphagia and adipsia, intragastric feeding is necessary in order to prevent drastic weight loss. The rats receive a daily gastric intubation of 2 g of the "modified rat tube feeding diet" (ICN Pharmaceuticals, Inc., Cleveland, Ohio, U.S.A.) mixed with approximately 2 ml tap water.

Ambulation in the open field is evaluated in an apparatus consisting of a wooden box (69 cm×69 cm×42 cm) with an arborite floor. The floor is divided into 36 squares (11.5 cm×11.5 cm). The placement of all four limbs in one square is taken as one ambulation score.

In the present experiments all compounds are evaluated four days after the intracerebral injection of 6-OHDA. The rat is placed into the center of the open field and observed for a 2-min period. Only rats with almost total akinesia are used. Apomorphine, bromocriptine or the compounds of formula I are injected s.c. to groups of 4–12 rats. Subsequently, the number of squares are counted which the animal entered during several 2-min observation periods. Apomorphine is evaluated at 5, 10, 15, 20 and 30 min; bromocriptine at 2, 3, 4, 5, 6 and 7 hr; and the compounds of formula I at 15, 30, 45, 60, 90 and 120 min after injection. Each animal is used only once. The results are expressed as cumulative number of ambulation scores, which are the sums of the scores obtained during the 2-min observation periods.

The following substances are used; apomorphine hydrochloride (Macfarlan Smith Ltd., Edinburgh, Scotland), bromocriptine (CB-154) (Sandoz Pharmaceuticals, East Hanover, N.J., U.S.A.) and 6-OHDA hydrobromide (Aldrich Chemical Co., Inc., Milwaukee, Wis., U.S.A.). The compounds are dissolved in distilled water or suspended in distilled water with a few drops of polysorbate 80 (Tween 80; "Tween" is a registered trade mark). If the compound is an oil, 0.4 ml of dimethyl sulfoxide is added. Solutions are prepared fresh on the day of the experiment. The 6-OHDA solution is kept in ice throughout the injection procedure. All doses refer to the base.

Using the above described method, apomorphine at a dose of 0.5 mg/kg exhibits a score of 135±41 and bromocriptine at a dose of 10 mg/kg exhibits a score of 112±23. Similarly, the following compound of formula I is an effective dopamine receptor agonist, 6,7,8,9-tetrahydro-N,N-dipropyl-3H-benz[e]indol-7-amine (at a subcutaneous dose of 2.5 mg/kg of body weight exhibited a cumulative ambulation score of 155±28).

The above described test methods for dopamine receptor agonists show that the compounds of formula I are active as dopamine receptor agonists. The compounds, thus, can be used clinically in the treatment of hyperprolactinemia, galactorrhoea, amenorrhea, impotence, diabetes, Parkinsonism, acromegaly, hypertension and other central nervous system disorders, which respond to dopamine-receptor stimulation.

The compounds of formula I of this invention are used alone or in combination with pharmacologically acceptable carriers, the proportion of which is determined by the solubility and chemical nature of the compound, chosen route of administration and standard biological practice. For example, they are administered orally in solid form i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as dopamine receptor agonists will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective dopamine receptor stimulating amount of the compounds for i.p. administration usually ranges from about 0.1 mg to about 250 mg per kilogram body weight per day in single or divided doses although as aforementioned variations will occur. However a dosage level that is in the range of from about 0.1 to about 100 mg per kilogram body weight per day in single or divided doses is employed most desirably for i.p. administration in order to achieve effective results. For oral administration, effective amounts can range from about 0.5 to about 250 mg per kilogram body weight per day in single or divided doses preferably about 1.0 to 50 mg per kilogram of body weight per day.

The compound of formula I, or a therapeutically acceptable salt thereof, also can be used to produce beneficial effects in the treatment of Parkinsonism, hyperprolactinemia and related disorders when combined with a therapeutically effective amount of an agent commonly used in the treatment of Parkinsonism, hyperprolactinemia and related disorders. Such agents include, for example, apomorphine and its derivatives, piribedil and its derivatives, dopaminergic ergot derivatives, especially bromocriptine and lergotrile, 2-amino-6,7-dihydroxy-(1,2,3,4)-tetrahydronaphthalene (ADTN), levodihydroxyphenylalanine (levodopa), combination of levodopa with carbidopa, L-prolyl-L-leucylglycinamide (MIF) and its derivatives, especially L-prolyl-N-methyl-D-leucylglycinamide (pareptide), biperiden, cycrimine hydrochloride, procyclidine, trihexyphenidyl hydrochloride, benztropine mesylate, chlorphenoxamine hydrochloride, diphenhydramine hydrochloride, orphenadrine hydrochloride, ethopropazine hydrochloride and the enzymes, monoamine oxidase B and catechol-O-methyl tranferase. A combination of the foregoing agents can be substituted for a single agent. Suitable methods of administration, compositions and dosages of the agents are well known in the art; for instance, "Physican Desk Reference", 32 ed., Medical Economics Co., Oradell, N.J., U.S.A., 1978. When used in combination, the compound of formula I, or its therapeutically acceptable salt, is administered as described previously.

Process

Reaction scheme 1 illustrates a method of preparing a diamine of formula II, an intermediate for the preparation of the compounds of formula I.

REACTION SCHEME 1

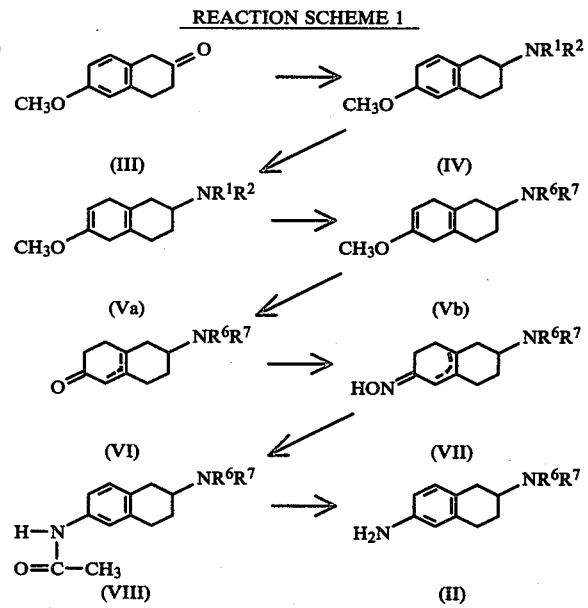

The starting material for the preparation of the intermediate of formula II is the 6-methoxy-2-tetralone of formula III. The compound of formula III is reacted with an excess of a di(lower alkyl)amine and about a molar amount of p-toluenesulfonic acid in an inert organic solvent, for example, benzene, at about 70° to 90°

C. for about one to five days and concurrent removal of water by azeotropic distillation. Reduction of the resulting enamine with hydrogen (about one to three atmospheres of pressure) in the presence of platinum oxide in ethanol gives the corresponding compound of formula IV in which $R^1$ and $R^2$ each is lower alkyl. Similarly, reaction of the compound of formula III with a lower alkyl amine, and reduction with sodium borohyride or catalytic hydrogenation of the resulting enamine gives the corresponding compound of formula IV in which $R^1$ is hydrogen and $R^2$ is lower alkyl. Another compound of formula IV is obtained by reaction of the compound of formula III with hydroxylamine to obtain the oxime, followed by reduction of the oxime with lithium aluminum hydride or nickel aluminum alloy gives the corresponding compound of formula IV in which $R^1$ and $R^2$ are hydrogen.

Alternatively, the compound of formula IV in which $R^1$ is hydrogen and $R^2$ is lower alkyl can be reacted with a N-alkylating agent to give the compound of formula IV wherein $R^1$ and $R^2$ each is lower alkyl.

hydrochloride in a solution of ethanol and pyridine at 20° to 30° C. for 20 to 40 hours gives the corresponding compound of formula VII in which $R^6$ and $R^7$ are as defined herein. Semmler-Wolff aromatization of the latter compound affords the corresponding compound of formula VIII in which $R^6$ and $R^7$ are as defined herein. The aromatization can be achieved by reacting the compound of formula VII with about two molar equivalents of acetic anhydride in acetic acid for about 20 minutes, adding hydrogen bromide and stirring the resultant solution at about 85° C. for about two hours. Another preferred method of aromatization involves the reaction of the compound of formula VII with acetyl chloride for about one hour at about 20° to 30° C. Hydrolysis of the compound of formula VIII with hydrochloric acid at about 100° C. for about one to five hours gives the corresponding diamine of formula II in which $R^6$ and $R^7$ are as defined herein.

Reaction scheme 2 illustrates a method for converting the compound of formula II to the compounds of formula I in which $R^4$ and $R^5$ are hydrogen.

REACTION SCHEME 2

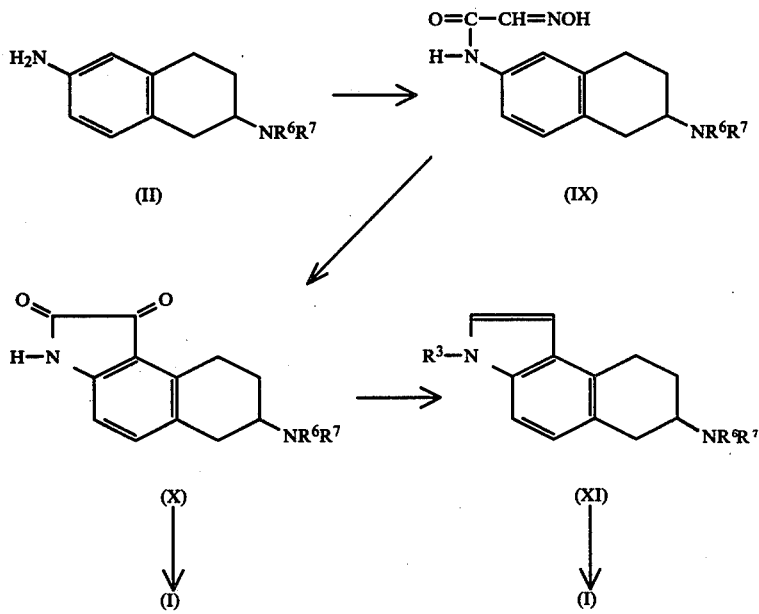

Reduction of the compound of formula IV in which $R^1$ and $R^2$ are as defined herein with sodium in a solution of tetrahydrofuran, isopropanol and liquid ammonia at about $-70°$ C. gives the corresponding compound of formula Va in which $R^1$ and $R^2$ are as defined herein. Reaction of the compound of formula Va in which $R^1$ is hydrogen and $R^2$ is hydrogen or lower alkyl with benzyl bromide, chloride or iodide gives the corresponding compound of formula Vb in which $R^6$ is benzyl and $R^7$ is benzyl or lower alkyl. The compound of formula Vb in which $R^6$ and $R^7$ each is lower alkyl is equivalent to the compound of formula Va in which $R^1$ and $R^2$ each is lower alkyl. The compound of formula Vb in which $R^6$ and $R^7$ each is benzyl or lower alkyl is subjected to acidic conditions, e.g. by dissolving the latter compound in a solution of acetone, diethyl ether and hydrochloric acid, and allowing the solution to stand at 20° to 30° C. for one to three hours, to obtain the corresponding compound of formula VI in which $R^6$ and $R^7$ are as defined herein. Reaction of the compound of formula VI with an excess of hydroxylamine With reference to reaction scheme 2, a solution of the compound of formula II, about three to four molar equivalents of hydroxylamine hydrochloride and about six to seven molar equivalents of sodium sulfate in about 5 percent hydrochloric acid is heated to about 100° C. and a solution of about 13 molar equivalents of chloral hydrate in water is added. The resulting solution is maintained at about 100° C. for about one to two hours to give the corresponding compound of formula IX in which $R^6$ and $R^7$ are as defined herein. Cyclization of the latter compound with concentrated sulfuric acid at about 0° to 80° C. for 0.5 to two hours gives the corresponding compound of formula X in which $R^6$ and $R^7$ are as defined herein.

Reduction of the compound of formula X in which $R^6$ and $R^7$ are lower alkyl with a complex metal hydride gives the corresponding compound of formula I in which $R^1$ and $R^2$ each is lower alkyl and $R^3$, $R^4$ and $R^5$ are hydrogen. This reduction can be achieved conveniently by reacting the compound of formula X with about ten molar equivalents of lithium aluminum hydride in an inert organic solvent, for example, tetrahydrofuran or diethyl ether, at 20° to 30° C. for 0.5 to ten hours to give the corresponding compound of formula I in which $R^1$ and $R^2$ each is lower alkyl and $R^3$, $R^4$ and $R^5$ are hydrogen. Alkylation of the latter compound of formula I gives the corresponding compound of formula I in which $R^1$, $R^2$ and $R^3$ each is lower alkyl and $R^4$ and $R^5$ are hydrogen. A convenient method of alkylation is the reaction of the compound of formula I with about one and a half to two molar equivalents of sodium amide (prepared from sodium in liquid ammonia containing ferric nitrate) in a mixture of diethyl ether and liquid ammonia to generate the corresponding anion. Reaction of this anion in the latter solvent system with a lower alkyl iodide, chloride or bromide for about one hour gives the corresponding compound of formula I in which $R^1$, $R^2$, $R^3$, $R^4$ and $R^5$ are as defined immediately above.

Similarly, reduction of the compound of formula X in which $R^6$ is benzyl and $R^7$ is benzyl or lower alkyl with the complex metal hydride gives the corresponding compound of formula XI in which $R^3$ is hydrogen, $R^6$ is benzyl and $R^7$ is benzyl or lower alkyl. Alkylation of the latter compound, in the same manner as described above, gives the corresponding compound of formula XI in which $R^3$ is lower alkyl, $R^6$ is benzyl and $R^7$ is benzyl or lower alkyl. Hydrogenation of the compound of formula XI in which $R^3$ is hydrogen or lower alkyl, $R^6$ is benzyl and $R^7$ is benzyl or lower alkyl in the presence of a noble metal hydrogenation catalyst, for example, platinum or carbon, palladium on carbon or platinum oxide, in an inert solvent, for example, methanol or ethanol, gives the corresponding compound of formula I in which $R^1$, $R^4$ and $R^5$ are hydrogen and $R^2$ and $R^3$ each is hydrogen or lower alkyl.

Reaction scheme 3 illustrates a method for converting the compound of formula II to the compounds of formula I in which $R^4$ and/or $R^5$ are lower alkyl.

REACTION SCHEME 3

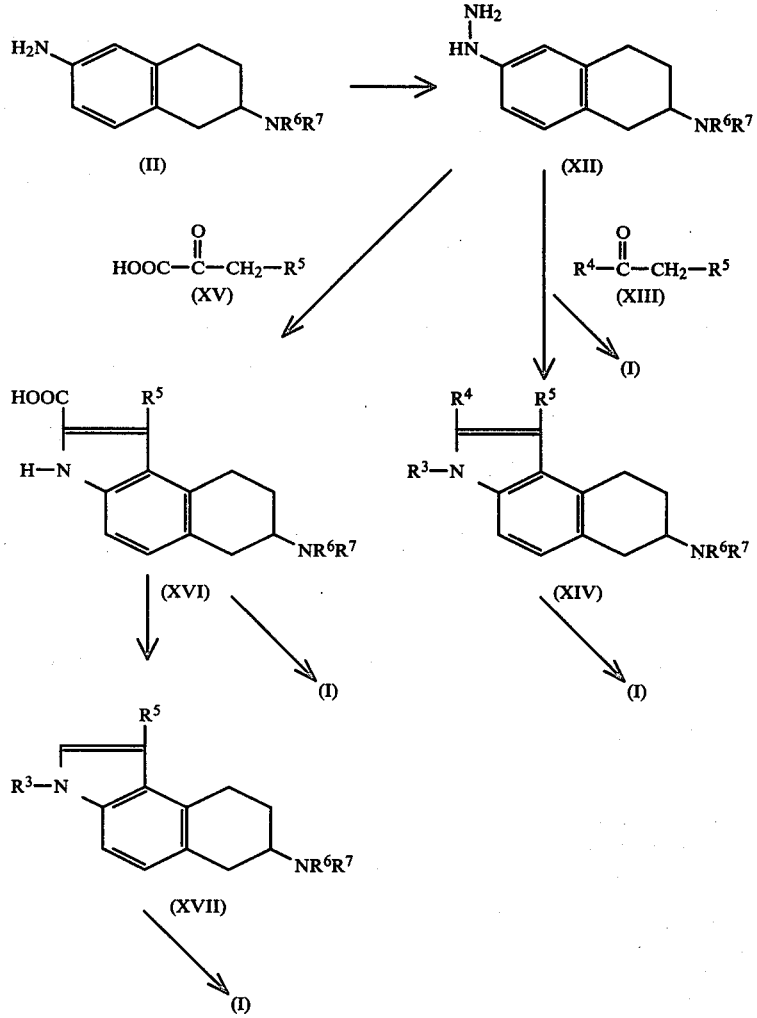

With reference to reaction scheme 3, the diamine of formula II in which $R^6$ and $R^7$ are as defined herein is converted to the corresponding hydrazide of formula XII in which $R^6$ and $R^7$ are as defined herein. For this conversion, a solution of the compound of formula II and about an equimolar amount of sodium nitrite in hydrochloric acid is maintained at about 0° C. for one to five hours. A solution of about two and half molar equivalents of stannous chloride is hydrochloric acid is added at about $-5°$ to $-15°$ C. The mixture is maintained at this temperature for about one to five hours.

Thereafter the corresponding compound of formula XII is isolated.

Condensation of the hydrazide of formula XII in which $R^6$ and $R^7$ each is lower alkyl with a ketone of formula XIII in which $R^4$ is lower alkyl and $R^5$ is hydrogen or lower alkyl according to the Fischer indole synthesis gives the corresponding compound of formula I in which $R^1$, $R^2$ and $R^4$ each is lower alkyl, $R^3$ is hydrogen and $R^5$ is hydrogen or lower alkyl. The indole synthesis is achieved by maintaining a solution of about equal molar quantities of the compounds of formulae XII and XIII in acetic acid at about 100° to 120° C. for about three to ten hours. Similarly, condensation of the compound of formula XII in which $R^6$ is benzyl and $R^7$ is benzyl or lower alkyl with the ketone of formula XIII in which $R^4$ is lower alkyl and $R^5$ is hydrogen or lower alkyl according to the Fischer indole synthesis gives the corresponding compound of formula XIV in which $R^3$ is hydrogen, $R^4$ is lower alkyl, $R^5$ is hydrogen or lower alkyl, $R^6$ is benzyl and $R^7$ is benzyl or lower alkyl. Alkylation of the latter compound, in the same manner as described above, gives the corresponding compound of formula XIV in which $R^3$ is lower alkyl and $R^4$, $R^5$, $R^6$ and $R^7$ are as defined immediately above. Hydrogenation of the compound of formula XIV in which $R^3$ is hydrogen or lower alkyl and $R^4$, $R^5$, $R^6$ and $R^7$ are as defined immediately above, in the same manner as described above, gives the corresponding compound of formula I in which $R^1$ is hydrogen, $R^2$, $R^3$ and $R^5$ each is hydrogen or lower alkyl and $R^4$ is lower alkyl.

A Fischer indole condensation of the compound of formula XII in which $R^6$ and $R^7$ are as defined herein with a keto-acid of formula XV in which $R^5$ is lower alkyl, in the same manner as described above, gives the corresponding compound of formula XVI in which $R^5$ is lower alkyl and $R^6$ and $R^7$ are as defined herein. Decarboxylation of the compound of formula XVI in which $R^6$ and $R^7$ each is lower alkyl, preferably with three to ten normal sulfuric acid at 50° to 100° C., yields the corresponding of formula I in which $R^1$, $R^2$ and $R^5$ each is lower alkyl and $R^3$ and $R^4$ are hydrogen. Similarly, decarboxylation of the compound of formula XVI in which $R^5$ is lower alkyl, $R^6$ is benzyl and $R^7$ is benzyl or lower alkyl gives the corresponding compound of formula XVII in which $R^3$ is hydrogen and $R^5$, $R^6$ and $R^7$ are as defined immediately above. The latter compound can be alkylated, in the same manner as described above, to give the corresponding compound of formula XVII in which $R^3$ is lower alkyl and $R^5$, $R^6$ and $R^7$ are as defined immediately above. Hydrogenation of the compound of formula XVII in which $R^3$ is hydrogen or lower alkyl and $R^5$, $R^6$ and $R^7$ are as defined immediately above, in the same manner as described above, gives the corresponding compound of formula I in which $R^1$ and $R^4$ are hydrogen, $R^2$ and $R^3$ each is hydrogen or lower alkyl and $R^5$ is lower alkyl.

If desired, the compounds of formula I in which $R^1$ and $R^2$ each is lower alkyl, $R^3$ is hydrogen and $R^4$ and $R^5$ each is hydrogen or lower alkyl can be alkylated, in the same manner as described above, to provide the corresponding compound of formula I in which $R^1$, $R^2$ and $R^3$ each is lower alkyl and $R^4$ and $R^5$ each is hydrogen or lower alkyl.

Also included within the scope of this invention are compounds of formula I having a halo substituent at position 2 or a lower alkyl substituent at position 6.

The following example illustrates further this invention.

EXAMPLE

Propylamine hydrochloride (169 g, 1.8 mol) was dissolved in methanol (370 mL) and 6-methoxy-2-tetralone (50 g, 0.28 mol) was added. Thereafter, sodium cyanoborohydride (44.2 g, 0.7 mol) was added portionwise with cooling. During the latter addition, the temperature of the reaction mixture was kept at 20° C. to minimize foaming. The resulting suspension was stirred at room temperature (25° C.) for 18 hr. Excess hydrochloric acid (1:1) was added and the white suspension was cooled in ice. The solid was collected on a filter and washed with methanol (3×200 mL) to give 92 g of crude product. The crude product was treated with 10% (w/v) sodium hydroxide and extracted with benzene. The organic extract was dried and evaporated to give a pale yellow oil (31.93 g) of N-propyl-6-methoxy-1,2,3,4-tetrahydro-2-naphthylamine, NMR (CDCl$_3$) δ 0.90 (t, 3H), 1.15 (s, 1H), 1.50 (m, 2H), 3.70 (s, 3H), 6.55 (s, 1H), 6.60 (d, 1H) and 6.90 (d, 1H).

Sodium borohydride (26.85 g, 0.71 mol) was added in small portions to propionic acid (172.2 mL, 2.3 moles) in dry benzene (650 mL), maintaining the temperature below 20° C. When hydrogen evolution ceased, a solution of N-propyl-6-methoxy-1,2,3,5-tetrahydro-2-naphthylamine (30.93 g, 0.141 mol) in benzene (150 mL) was added and the resulting mixture was refluxed for 3 hr. The cooled mixture was shaken with excess 10% (w/v) sodium hydroxide solution. The organic layer was separated, dried over MgSO$_4$ and evaporated to give a brown oil of N,N-dipropyl-6-methoxy-1,2,3,4-tetrahydro-2-naphthylamine, NMR (CDCl$_3$) δ 0.85 (t, 6H), 1.45 (m, 6H), 2.45 (t, 4H), 2.7 (m, 5H), 3.70 (s, 3H) and 6.7 (m, 3H).

A solution of N,N-dipropyl-6-methoxy-1,2,3,4-tetrahydro-2-naphthylamine (17.6 g, 0.067 mole) in tetrahydrofuran (188 mL) and isopropanol (188 mL) was added with stirring to liquid ammonia (500 mL) cooled by a dry ice-isopropanol bath. Sodium (29.4 g, 1.3 g-atom) was added in small pieces over 0.5 hr. After the blue colour disappeared (ca. 2 hr), methanol (120 mL) was added and the ammonia was allowed to evaporate after removal of the cooling bath. The residue was diluted with water (1000 mL) and extracted three times with diethyl ether. The ether extracts were dried (MgSO$_4$) and concentrated, giving a yellow oil (15.8 g) of 1,2,3,4,5,8-hexahydro-6-methoxy-N,N-dipropyl-2-naphthalenamine, NMR (CDCl$_3$) δ 0.85 (t, 6H), 3.5 (s, 3H) and 4.6 (m, 1H).

A solution of 1,2,3,4,5,8-hexahydro-6-methoxy-N,N-dipropyl-2-naphthalenamine (32.5 g, 0.12 mole) in a mixture of acetone (542 mL), water (72 mL) and diethyl ether saturated with hydrogen chloride (270 mL) was stirred at room temperature for 3 hr, basified with sodium carbonate and extracted with diethyl ether. The ether extracts were dried (MgSO$_4$) and concentrated giving a mixture of 6-(N,N-dipropylamino)-2,3,4,4a,5,6,7,8-octahydronaphalen-2-one and 6-(N,N-dipropylamino)-1,2,3,4,5,6,7,8-octahydronaphalen-2-one as a brown oil (22.3 g): NMR (CDCl$_3$) δ 0.85 (t, 6H) and 5.75 (s, 1H) and IR (CHCl$_3$)1705 1660 and 1615 cm$^{-1}$.

A solution of the latter mixture (22.0 g, 0.088 mL) and hydroxylamine hydrochloride (21.7 g) in ethanol (208 mL) and pyridine (197 mL) was stirred at room temperature for 18 hr. The mixture was concentrated, dissolved in water, basified with excess sodium bicarbonate and extracted into chloroform. The extract was dried (MgSO$_4$) and concentrated to give a red oil (22.7 g) of 6-(N,N-dipropylamino)-2,3,4,4a,5,6,7,8-octahydronaphthalen-2-oxime and 6-(N,N-dipropylamino)-1,2,3,4,5,6,7,8-octahydronaphalen-2-oxime; NMR (CDCl$_3$) δ 0.95 (t, 6H), 5.9 and 6.6 (singlets, 1H).

Acetic anhydride (15.7 mL, 0.166 mole) was added to a stirred solution of the latter mixture of oximes (22.1 g, 0.083 mole) in acetic acid (175 mL). The mixture was stirred at 35° C. for 30 min and anhydrous gaseous hydrogen bromide was slowly passed through the solution until a temperature of 78° C. was attained. The flow of hydrogen bromide was stopped and the dark solution was stirred at 85° C. for 2 hr. After cooling, the solution was concentrated under reduced pressure and a sodium carbonate solution (~200 mL) was added to the reaction mixture until the pH became basic. The product was extracted with ethyl acetate. The organic extract was dried over MgSO$_4$, treated with charcoal, filtered through diatomaceous earth and evaporated to dryness to afford a brown oil (18.2 g) and N-[6-(N,N-dipropylamino)-5,6,7,8-tetrahydro-2-naphthalenyl]acetamide. A sample (2.44 g) was treated with acetic anhydride (8.5 mL) and pyridine (7.3 mL) at room temperature for 18 hr. The reaction mixture was evaporated to dryness and partitioned between water and ethyl acetate. The aqueous phase was basified with potassium carbonate and extracted with ethyl acetate to afford a solid compound (1.62 g) which crystallized out of benzene and hexane to give a brown solid (723 mg) of N-[6-(N,N-dipropylamino)-5,6,7,8-tetrahydro-2-naphthalenyl]acetamide, mp 119°–121° C. and NMR (CDCl$_3$) δ 0.85 (t, 6H), 1.4 (m, 6H), 2.10 (s, 3H) and 6.8 to 7.3 (m, 3H).

A mixture of N-6-(dipropylamino)-5,6,7,8-tetrahydro-2-naphthalenyl]acetamide (13.78 g, 0.057 mole) in 2 N hydrochloric acid (37 mL) was refluxed for 2 hr. After cooling, the solution was basified with 1 N sodium hydroxide and extracted four times with benzene. The organic extracts were dried (MgSO$_4$) and concentrated to afford a red oil (9.81 g) of 1,2,3,4-tetrahydro-N$^2$,N$^2$-dipropyl-2,6-naphthalenediamine: NMR (CDCl$_3$) δ 0.85 (t, 6H), 1.0 to 3.0 (m, 15H), 5.3 (b, 2H) and 6.3 to 7.5 (m, 3H).

1,2,3,4-Tetrahydro-N$^2$, N$^2$-dipropyl-2,6-naphthalenediamine (8.81 g, 0.035 mole) was dissolved in diethyl ether and a solution of hydrogen chloride in diethyl ether was added. The solution was evaporated and the residue was dissolved in water (108 mL). Hydroxylamine hydrochloride (8.27 g, 0.117 mole) and anhydrous sodium sulfate (34.14 g, 0.234 mole) was added. The mixture was brought to a boil, and immediately, a boiling solution of chloral hydrate (7.34 g) in water (108 mL) was added. The combined mixture was boiled for one hr, cooled and diluted with ammonium hydroxide (20 mL of conc. ammonium hydroxide in 200 mL water). The mixture was extracted with ethyl acetate (3x) and the ethyl extracts were combined, dried and evaporated to dryness to afford a brown solid (6.0 g) which was chromatographed through a column of silica gel (180 g) using chloroform and 1 and 10% methanol-chloroform (v/v). The appropriate eluates were evaporated and the residue was crystallized from dichloromethane-hexane to give N-[6-(dipropylamino)-5,6,7,8-tetrahydro-2-naphthalenyl]-2-(hydroxyimino)acetamide, mp 110°–112° C.; NMR (CDCl$_3$) δ 0.90 (t, 6H), 1.51 (m, 6H), 6.95 (s, 2H), 7.20 (s, 1H), 7.50 (s, 1H), 8.0 (s, 1H) and 10.3 (b, 1H); and Anal. Calcd for C$_{18}$H$_{27}$N$_3$O: C, 68.10% H, 8.57% N, 13.23% and Found: C, 67.81% H, 8.50% N, 13.20%.

N-[6-(Dipropylamino)-5,6,7,8-tetrahydro-2-naphthalenyl]-2-(hydroxyimino)acetamide (1.49 g, 4.7 mmole) was added at 0° C. to a rapidly stirred solution of concentrated sulfuric acid (24 mL). After stirring for one hr at 0° C., the reaction mixture was warmed to room temperature for 2 hr and poured onto ice-water (200 mL). The mixture was basified with concentrated ammonium hydroxide (80 mL) and extracted with ethyl acetate. The organic extracts were dried (MgSO$_4$) and evaporated to dryness to afford a red foam (1.49 g) which was chromatographed through silica gel using chloroform and 1 to 10% methanol-chloroform (v/v). Evaporation of the eluates afforded 6,7,8,9-tetrahydro-7-(dipropylamino)-3H-benz[e]indole-1,2-dione (1.07 g) which was crystallized from diethyl ether-hexane: mp 83°–86° C.; NMR (CDCl$_3$) δ 0.85 (t, 6H), 1.45 (m, 6H), 1.7–3.6 (m, 9H), 6.60 (d, 1H) and 7.15 (d, 1H); and Anal. Calcd for C$_{18}$H$_{24}$N$_2$O$_2$. 5.29% H$_2$O: C, 68.16% H, 8.21% N, 8.83% and Found: C, 68.28% H, 8.11% N, 8.99%.

To a cooled suspension of lithium aluminum hydride (3.2 g, 84.3 mmoles) in tetrahydrofuran (215 mL) under nitrogen was added dropwise a solution of 6,7,8,9-tetrahydro-7-(dipropylamino)-3H-benz[e]indole-1,2-dione (2.5 g, 8.32 mmole) in tetrahydrofuran (50 mL) and the mixture was stirred at room temperature for 2 hr. The excess of lithium aluminum hydride was destroyed at 0° C. by careful addition of a 10% (v/v) mixture of water in tetrahydrofuran (50 mL). The inorganic salts were filtered off through diatomaceous earth and washed with tetrahydrofuran. The filtrate was concentrated and water was added. The product was extracted in diethyl ether. The organic extracts were dried (MgSO$_4$) and concentrated to dryness to afford a blue oil (1.75 g) which was chromatographed through a column of silica gel (110 g) using 3% methanol-diethyl ether (v/v). Evaporation of the eluates gave 0.518 g of 6,7,8,9-tetrahydro-N,N-dipropyl-3H-benz[e]indol-7-amine, which was crystallized from methanol-water to give crystals (0.344 g) of the latter compound of formula I: mp 101°–104° C.; NMR (CDCl$_3$) δ 0.9 (t, 6H), 1.50 (m, 6H), 2.05–3.05 (m, 9H), 6.45 (m, 1H), 7.0 (m, 3H) and 8.1 (b, 1H); and Anal. Calcd for C$_{18}$H$_{26}$N$_2$: C, 79.94% H, 9.69% N, 10.36% and Found: C, 80.07% H, 9.76% N, 10.31%.

We claim:

1. A compound of the formula

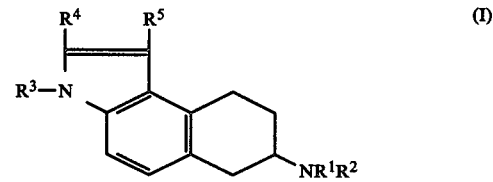

wherein R$^1$ and R$^2$ each is hydrogen or lower alkyl having 1 to 5 carbon atoms and R$^3$, R$^4$ and R$^5$ are hydrogen, or a therapeutically acceptable acid addition salt thereof.

2. A compound of claim 1 wherein R$^1$ and R$^2$ each is lower alkyl having 1 to 3 carbon atoms and R$^3$, R$^4$ and R$^5$ are hydrogen, or a therapeutically acceptable acid addition salt thereof.

3. 6,7,8,9-Tetrahydro-N,N-dipropyl-3H-benz[e]indol-7-amine, a compound of claim 1 wherein $R^1$ and $R^2$ are propyl and $R^3$, $R^4$ and $R^5$ are hydrogen.

4. A compound of the formula

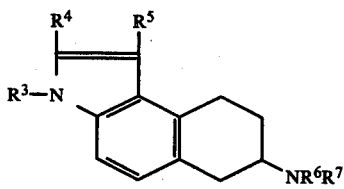

in which $R^3$, $R^4$ and $R^5$ each is hydrogen, $R^6$ is benzyl and $R^7$ is benzyl or lower alkyl.

5. A pharmaceutical composition for stimulating dopamine-receptors, which comprises a therapeutically effective amount of a compound of claim 1, or a therapeutically acceptable acid addition salt thereof, and a pharmaceutically acceptable carrier therefor.

6. A method of stimulating dopamine-receptors in a mammal in need thereof, which comprises administering to said mammal an effective dopamine receptor stimulating amount of a compound of claim 1 or a therapeutically acceptable acid addition salt thereof.

* * * * *